(12) United States Patent
Mayeaux (10) Patent No.: US 7,555,964 B2
(45) Date of Patent: Jul. 7, 2009

(54) PHASE SEPARATION SYSTEM AND HOUSING THEREFORE

(75) Inventor: Donald P. Mayeaux, St. Amant, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 853 days.

(21) Appl. No.: 10/940,006

(22) Filed: Sep. 13, 2004

(65) Prior Publication Data

US 2005/0061720 A1 Mar. 24, 2005

Related U.S. Application Data

(63) Continuation-in-part of application No. 10/631,502, filed on Jul. 31, 2003, now Pat. No. 7,097,693.

(60) Provisional application No. 60/400,736, filed on Aug. 2, 2002.

(51) Int. Cl.
*F16K 25/02* (2006.01)
*B01D 61/00* (2006.01)
*G01N 1/18* (2006.01)
*G01N 1/20* (2006.01)
*G01N 1/34* (2006.01)

(52) U.S. Cl. .................. 73/863.02; 73/863.23; 210/97; 210/321.75

(58) Field of Classification Search . 73/863.02–863.03, 73/863.23, 863.61; 210/97, 109, 321.6, 321.72, 210/321.75, 321.84, 435, 541; 251/335.2
See application file for complete search history.

(56) References Cited

U.S. PATENT DOCUMENTS

| | | | | |
|---|---|---|---|---|
| 3,186,917 A | * | 6/1965 | Gerhardt et al. ....... | 210/321.6 X |
| 4,014,216 A | * | 3/1977 | Thornton et al. ......... | 73/863.23 |
| 4,112,768 A | * | 9/1978 | Holland et al. .......... | 73/863.24 |
| 4,360,433 A | * | 11/1982 | Walker et al. ............... | 210/484 |
| 4,437,986 A | * | 3/1984 | Hutchins et al. ............ | 210/130 |
| 4,477,345 A | * | 10/1984 | Szlaga, Jr. ................... | 210/130 |
| 5,442,969 A | * | 8/1995 | Troutner et al. ....... | 73/863.02 X |
| 5,800,597 A | * | 9/1998 | Perrotta et al. .................... | 96/9 |
| 5,841,036 A | * | 11/1998 | Mayeaux ..................... | 73/863 |
| 5,844,123 A | * | 12/1998 | Marsh et al. ............... | 73/19.12 |
| 6,357,304 B1 | * | 3/2002 | Mayeaux ................. | 73/863.23 |
| 7,134,318 B2 | * | 11/2006 | Mayeaux ................... | 73/29.01 |
| 2005/0178718 A1 | * | 8/2005 | Geibel et al. ................ | 210/456 |

FOREIGN PATENT DOCUMENTS

JP  04108589 A * 4/1992 ................. 210/188

* cited by examiner

*Primary Examiner*—Thomas P Noland
(74) *Attorney, Agent, or Firm*—Joseph T. Regard, Ltd plc (57) ABSTRACT

A method and apparatus for the physical separation of components from a multi-phase fluid stream into its component phases. More particularly, the invention relates to a housing for a phase separation medium which allows one to change the phase separation medium without the necessity of disconnecting the flow lines. An alternative embodiment of the present invention contemplates a housing incorporating a unique internal valve configuration for controlling and limiting the fluid pressure differential across the sheet of phase-separating material. The internal valve begins to throttle or reduce the fluid flow rate through the sheet of phase-separating material after the differential pressure across the sheet of phase-separating material exceeds a preset value. If throttling the fluid flow rate cannot prevent the differential pressure from exceeding the preset limit, then the internal valve will shut off the fluid flow completely.

42 Claims, 7 Drawing Sheets

PHASE SEPARATION SYSTEM AND HOUSING THEREFORE

STATEMENT OF CONTINUING APPLICATION

This application is a continuation-in-part of U.S. patent application Ser. No. 10/631,502 filed Jul. 31, 2003 and issued Aug. 29, 2006 as U.S. Pat. No. 7,097,693, entitled "Combination Depth and Phase Separation Membrane Filter", which '693 patent claims the benefit of U.S. Provisional Patent Application 60/400,736, filed on Aug. 2, 2002.

TECHNICAL FIELD of the INVENTION

The present invention relates to method and apparatus for the physical separation of components from a multi-phase fluid stream into its component phases. More particularly, the invention relates to systems for housing for a phase separation medium which allow external access to the phase separation medium, without the necessity of disconnecting the flow lines channeled through the housing.

An embodiment of the present system also contemplates a phase separation housing incorporating a unique internal valve configuration for controlling and limiting the fluid pressure differential across the sheet of phase-separating material.

The internal valve configuration is configured to shut off the fluid flow completely to maintain the phase separation medium within established operational parameters where throttling the fluid flow rate does not prevent the differential pressure from exceeding the preset limit.

BACKGROUND OF THE INVENTION

Depending upon the application, generally it is important bring a fluid into intimate contact with the surface of the filter medium during filtering. This is particularly true when a membrane separator are employed in the filtration process. A membrane separator can function in a manner that filters out particulates, separates liquids from gases, and in some cases separate immiscible liquids from one another.

A common technique employed when sampling a fluid stream under pressure, particularly in analytical applications, is to have the fluid enter a housing, and have a portion of the fluid entering the housing bypass the filter medium. This procedure is followed in order to decrease transport time and purge incoming sample lines.

This procedure also serves, in many cases, to remove some of the materials that were separated from the incoming fluid by the filter medium. This is particularly so in membrane separators, wherein liquids are rejected by the membrane and are swept out with the bypass stream.

Utilizing this technique, it is also possible to remove particulates continuously as they accumulate on the surface of the filter medium or membrane. The filtrate leaves the housing through an outlet port. In the case of analyzers, the sample may be further conditioned after passing through the filter medium or membrane before being sent to an analyzer.

Past filter designs often have unnecessary internal volume, which provides problems in use. It would be desirable, particularly in analytical applications, to keep the internal volume of a filter housing at a minimum and configure the internal volume free of unpurged areas or "dead volume". Another desirable characteristic of a filter housing would be to provide easy access to the filter medium.

For safety and environmental reasons, it would be highly desirable that the filter medium be accessible without disconnecting any of the fluid lines attached to the filter housing.

Other prior designs have offered poor performance due to inconsistent pressure differentials applied across the filter medium. In cases where phase separating membrane are employed, it is therefore important to limit the pressure differential across the membrane. If the pressure difference between the upstream and downstream sides of the membrane exceed certain values (which may vary with individual application), then some liquid which would be otherwise rejected will pass through the membrane, and the phase separation membrane will not perform as designed.

Accordingly, it is desirable to provide a sample system in such a manner that will minimize the risk of exceeding recommended membrane differential pressures.

It can be a costly and difficult task to design sample systems in the manner required to prevent excessive membrane differential pressures from occurring under all conditions. Further, this process is not well understood by all who design sample systems.

For example, a system that maintains a suitable membrane differential pressure under normal circumstances may not prevent excessive membrane differential pressures from occurring during upset conditions. This is a frequent occurrence which allows some of the undesired liquid to flow through the membrane. The net result could be that an analyzer is damaged and/or analysis compromised.

One type of current art housing is comprised of two plates arranged to hold the sheet of filter media or membrane between the interior plate surfaces in a parallel configuration. The plates are held together with bolts or screws. Refer to Mayeaux U.S. Pat. No. 5,476,586. The fluid entry, exit, and bypass ports are distributed on both plates.

This type of construction requires detachment of one or more fluid lines from the housing in order to access the membrane, which by necessity interrupts the flow of fluid through the housing. In many cases this presents safety and environmental hazards.

Another type of current art housing is comprised of a hollow body, filter media holder and cover. The entry, exit, and bypass ports are all located in the body segment of the housing. The filter media or membrane is retained in the holder segment which is inserted into the body segment. The cover is threadingly engaged to the body segment and retains the media holder inside of the body segment.

This type of three-piece construction is more expensive to manufacture and requires the removal of two housing parts to access the filter media or membrane.

GENERAL SUMMARY DISCUSSION OF THE INVENTION

Unlike the prior art, the present invention provides a phase separation system which provides easy access to the filter medium without the necessity of detaching any fluid lines, nor does it entail an expensive or complicated housing design, providing a system which is more effective, safer, and easier to operate and maintain than the prior art.

Figure 1A:
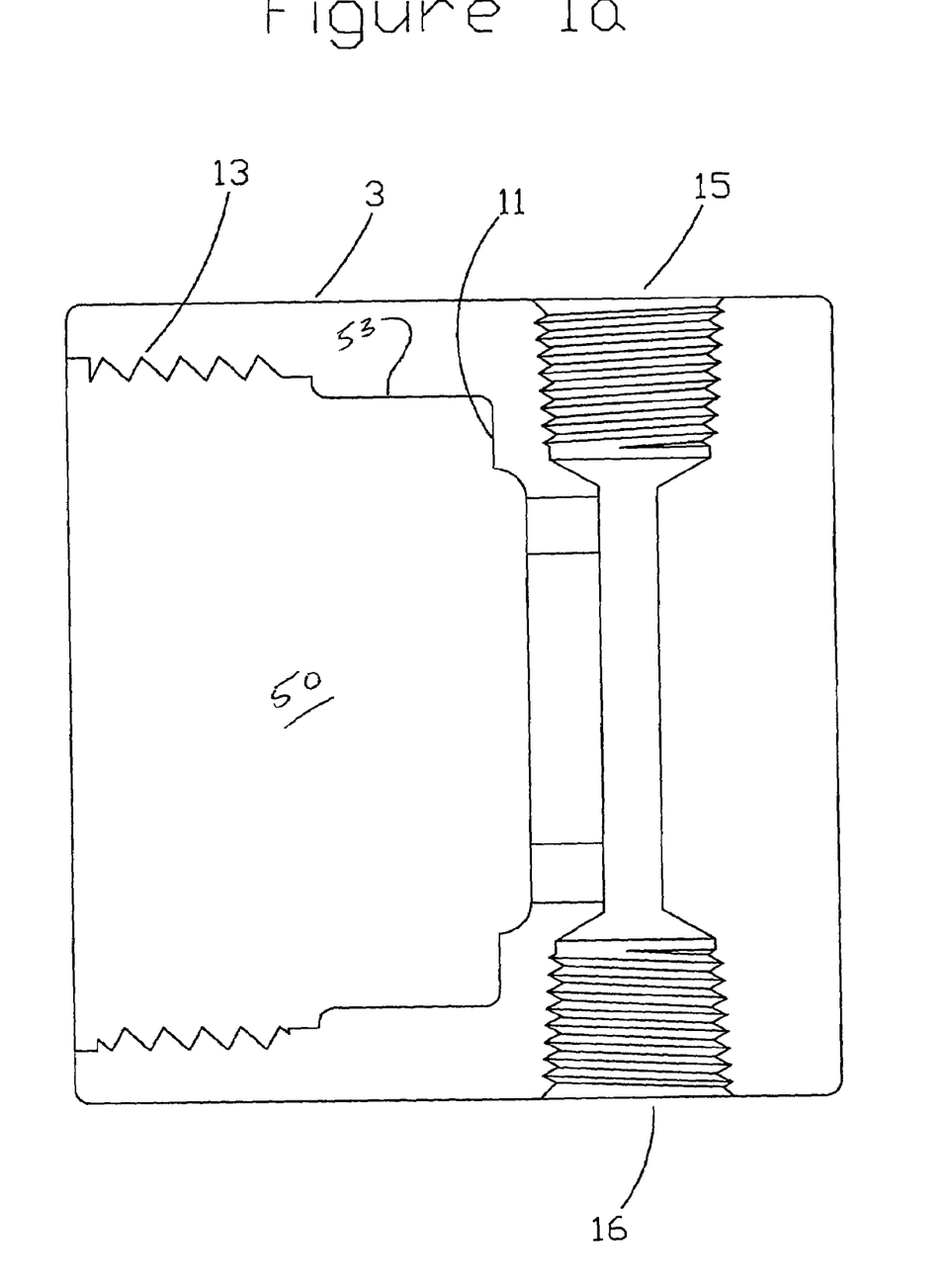
FIG. 1 is a side, cut-away view of the body of the present invention showing the inlet and bypass ports.
Figure 1B:
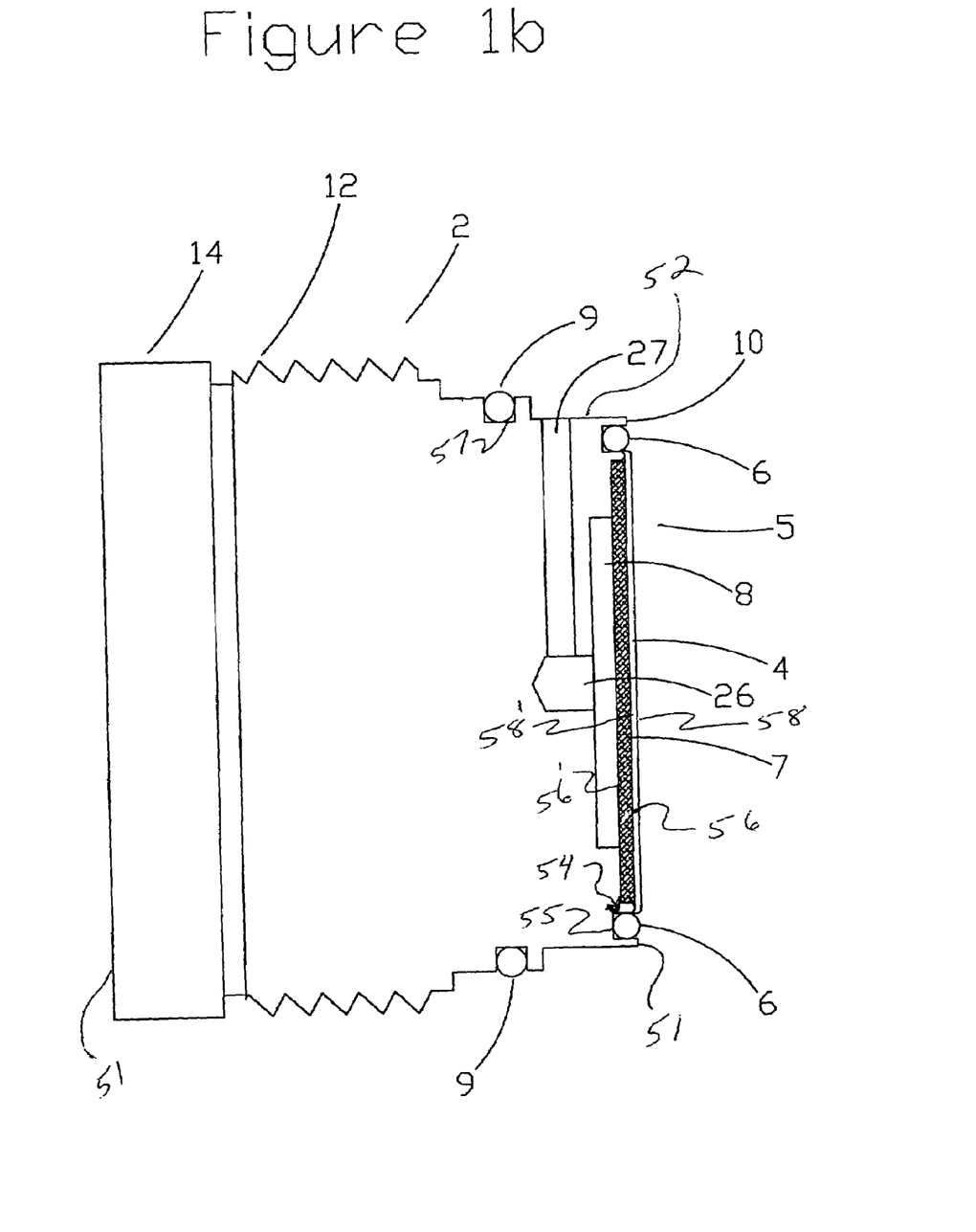
FIG. 1b is a side, partially cut-away view of the cover formed to threadingly engage the body of FIG. 1A, to form the housing of the present invention.
Figure 2:
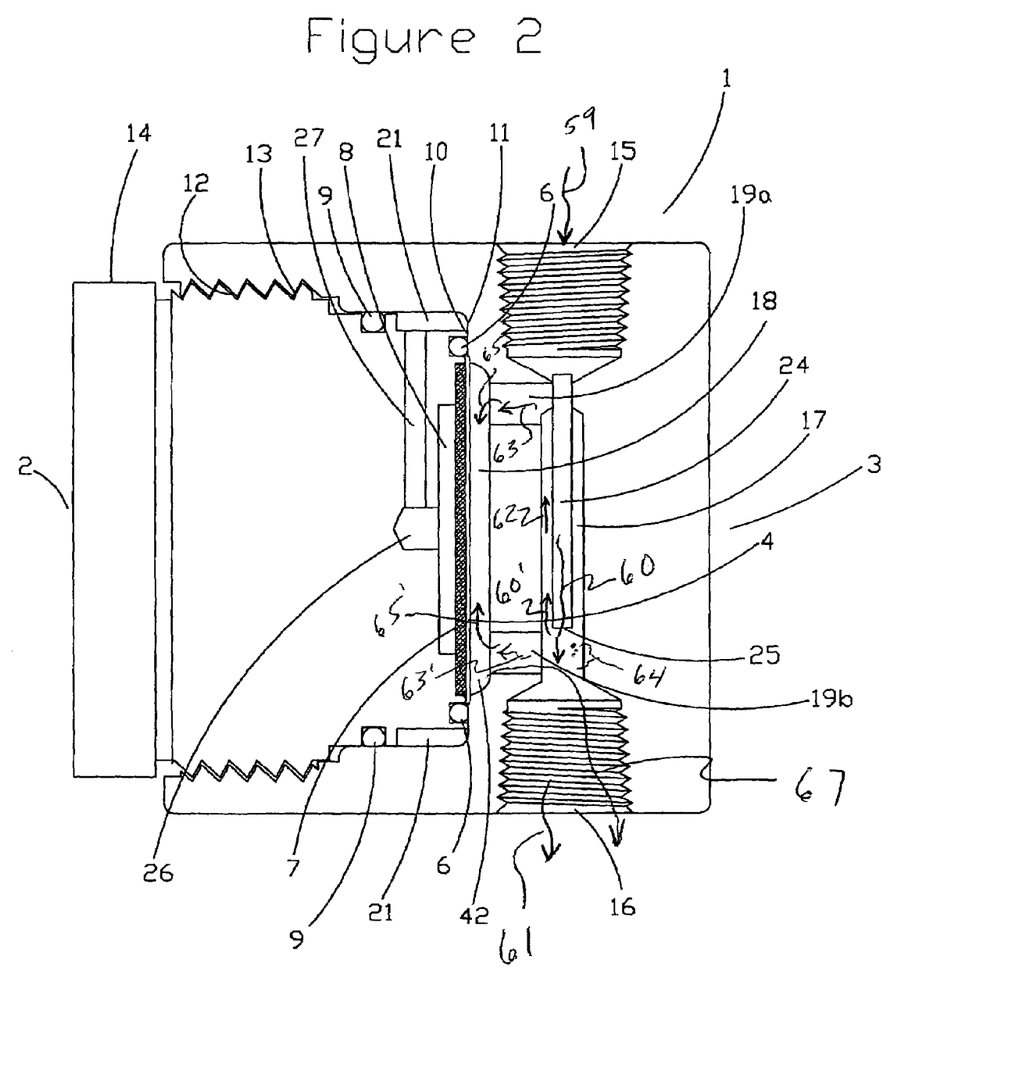
FIG. 2 is a side, partially cut-away view of the housing of the present invention illustrating the assembled cover and body, with inlet and bypass ports shown.

In general, the present invention provides unique design for a housing for a sheet of phase separating material. The housing is comprised of a hollow body (FIG. 1a) and a cover (FIG. 1b). The cover segment is thredly engaged to the body (FIG. 2). The sheet of phase-separating material is attached to the interior surface of the cover.

When assembled as shown in FIG. 2, the sheet of phase-separating material is disposed parallel and in close proximity to the interior bottom surface of the body. Threaded ports accommodate the flow of fluid into and out of the body.

Fluids flowing through the sheet of phase-separating material are provided a path to the outlet port by a channel formed in the space between the outside diameter of one end of the cover and the inside diameter at the bottom of the body sample cavity.

A sheet of phase-separation material is held in place by an o-ring and is supported by a porous or perforated plate in the direction of fluid flow.

Figure 4:
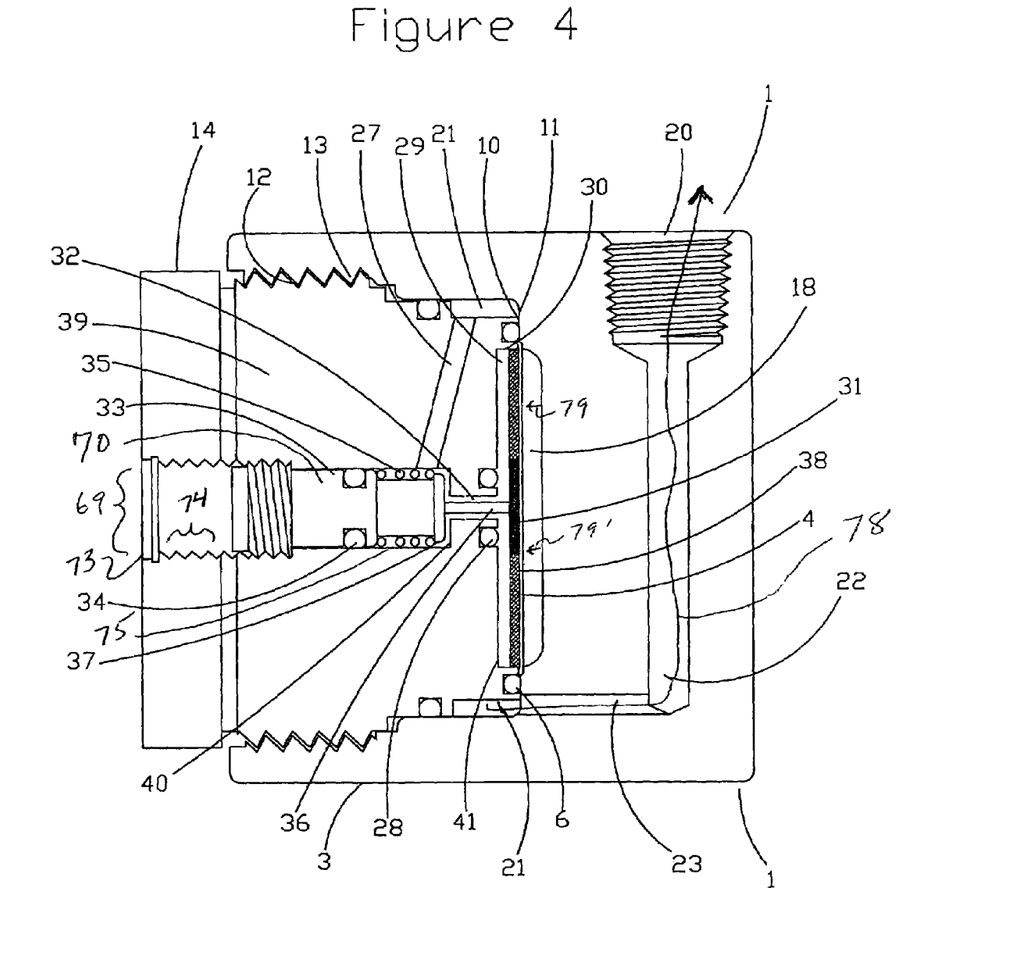
FIG. 4 is a side, cut away view of an alternative embodiment of the present invention utilizing the body of FIG. 1, but a cover having a valve, wherein said is shown in an open position.

A second embodiment of the present invention has an internal valve for controlling and limiting the fluid pressure differential across the sheet of phase-separating material. Refer to FIG. 4.

Said internal valve is actuated by the force developed from the fluid differential pressure acting on the surface of the sheet of phase-separating membrane. In a preferred embodiment, the internal valve consist of a flat surface applied across the surface of an o-ring comprising a "flat faced" o-ring seal. A second embodiment of the internal valve consists of a metal-to-metal seal (not shown).

The internal valve begins to throttle or reduce the fluid flow rate through the sheet of phase-separating material after the differential pressure across the sheet of phase-separating material exceeds a preset value.

This will typically occur as a result of excessive fluid flow rates through the sheet of phase-separating material. If throttling the fluid flow rate cannot prevent the differential pressure from exceeding the preset limit, then the internal valve will shut off the fluid flow completely. This can occur when liquid fills completely or almost completely the sample cavity upstream of the sheet of phase-separating material.

It is therefore an object of the present invention to provide a housing for a phase separation medium which allows one to change the phase separation medium without disconnecting the flow lines.

It is another object of the present invention to provide a phase separation housing which provides easy access to the phase separation medium It is still another object to provide a phase separation housing which is relatively easy to manufacture and more effective than the prior art.

It is still another object to provide a system for phase separation of a multi-phase fluid stream which is safer and more reliable than prior art systems.

It is still another object to provide a system for phase separation of a multi-phase fluid stream which utilizes two primary parts.

It is still another object of the present invention to provide a phase separation housing which requires less parts, is less expensive to manufacture and utilize, and which is more reliable in operation than prior art systems.

It is still another object of the present invention to provide a method and system for phase separation incorporating an internal valve configured to reduce the fluid flow rate through the sheet of phase-separating material after the differential pressure across the sheet of phase-separating material exceeds a preset value Lastly, it is an object of the present invention to provide a method and system for phase separation employing a housing having an internal valve for controlling and limiting the fluid pressure differential across the sheet of phase-separating material.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DETAILED DISCUSSION OF THE INVENTION

Referring to FIGS. 1A, 1B and 2, 4 and 5, a housing 1 is provided comprising a body 3 having a main cavity 50 formed therein configured to receive a cover 2, said cover having first 51 and second 51' ends, and an outer perimeter 52 configured to engage the inner diameter 53 of the main cavity 50. A sheet of phase-separating material 4 having first 58 and second 58' sides is held in place across at least a portion of the surface 5 of the first end 51 of cover 2 by retention o-ring 6, which retains the outer edge 54 of the phase-separating material 4 within groove 55 formed in the first end 51 of cover and which seals the first end 51 of cover about the sample cavity 18 formed in body, providing a sealed area where fluid in sample cavity 18 is directed to pass through phase-separating material 4 (or other designated filtration media).

The sheet of phase-separating material 4 is preferably a phase-separating membrane, but could also consist of any other filtration media. The first side 56 of a perforated or porous support plate 7 engages the second side 58' of the phase-separating material, supporting said phase-separating material 4 in the direction of fluid flow.

A sample cavity 8 is formed in the cover 2 behind and adjacent to the second side 56' of the support plate 7. An O-ring 9 situated in groove 57 provides a fluid seal about the outer perimeter 52 of the cover 2 and the internal diameter 53 of the main cavity 50 formed in the body 3 (FIG. 2).

In addition to retaining the sheet of phase-separating material 4, retention O-ring 6 also forms a fluid seal between the lower end surface 10 of cover 2 and the interior surface 11 of body 3, so as to form a fluid passage cavity 21 formed by the spacing between the outside diameter of the cover and the inside diameter of the cavity within the body, or stated another way, the fluid passage cavity is situated about the outer perimeter of cover, enveloped by body, and sealed with with O-ring. Preferably, O-rings 9 and 6 are made of an elastomeric material. As will be shown, the fluid passage cavity allows for the passage of filtered fluid, which has passed through the sheet of phase separating material of other filtration medium, to pass to the outlet port of the unit.

Cover 2 and body 3 are held together by the threaded engagement of male thread 12 formed on the exterior surface of cover 2 and female thread 13 formed on the inside surface of body 3.

Hand grip 14 formed in cover 2 provides a means for threadingly engaging or screwing cover 2 into body 3. Inlet port 15, bypass port 16, and sample cavity 18 are formed in the body 3 and fluidly interconnected by inertial tube 24, passage 17 and passages 19a and 19b, formed in the body. Outlet port 20 (FIGS. 4 and 5) formed in body is fluidly connected to cavity 21 (formed in cover and body and sealed by o-rings 6, 9) by way of passages 22 and 23, formed in body.

The assembled cover 2 and body 3 to form housing 1 provides a device for separating a multiphase feed stream into its component phases. In use, the sheet of phase-separating material 4 may be a filter paper or filter leaf, and the multiphase feed stream may comprise a suspension of a solid phase in a liquid phase. Alternatively, a sheet of phase-separating material 4 may be a membrane capable of separating two immiscible liquid phases. A third type of feed stream is represented by gas and liquid phases, in which case the sheet of phase-separating material 4 would be a membrane capable of separating the gas and liquid phases.

Continuing with FIGS. 1a, 1b, 2 and 3, 4 and 5, in use, incoming sample fluid enters 59 the housing 1 through inlet port 15 and thereafter flows 60, 60' through inertial tube 24 and into bypass port 16 and passage 17, respectively. A portion of the fluid flows 61 out of the housing through bypass port 16, providing a bypass stream. The primary purpose of the bypass fluid stream is to bring fresh or current fluid sample quickly into passage 17.

A second portion of fluid flowing from inertial tube end 25 reverses 60' its direction and flows 62 into passage 17 and thereafter flows 63, 63' to passages 19a and 19b (respectively) into 65, 65' sample cavity 18. The fluids abrupt reversal of flow direction (60') at the end 25 of the inertial tube 24 provides a degree of inertial pre-separation of particles which are heavier than the principle sample fluid, which separated particles 64 flow 61 out of the housing through bypass port 16.

Figure 3:
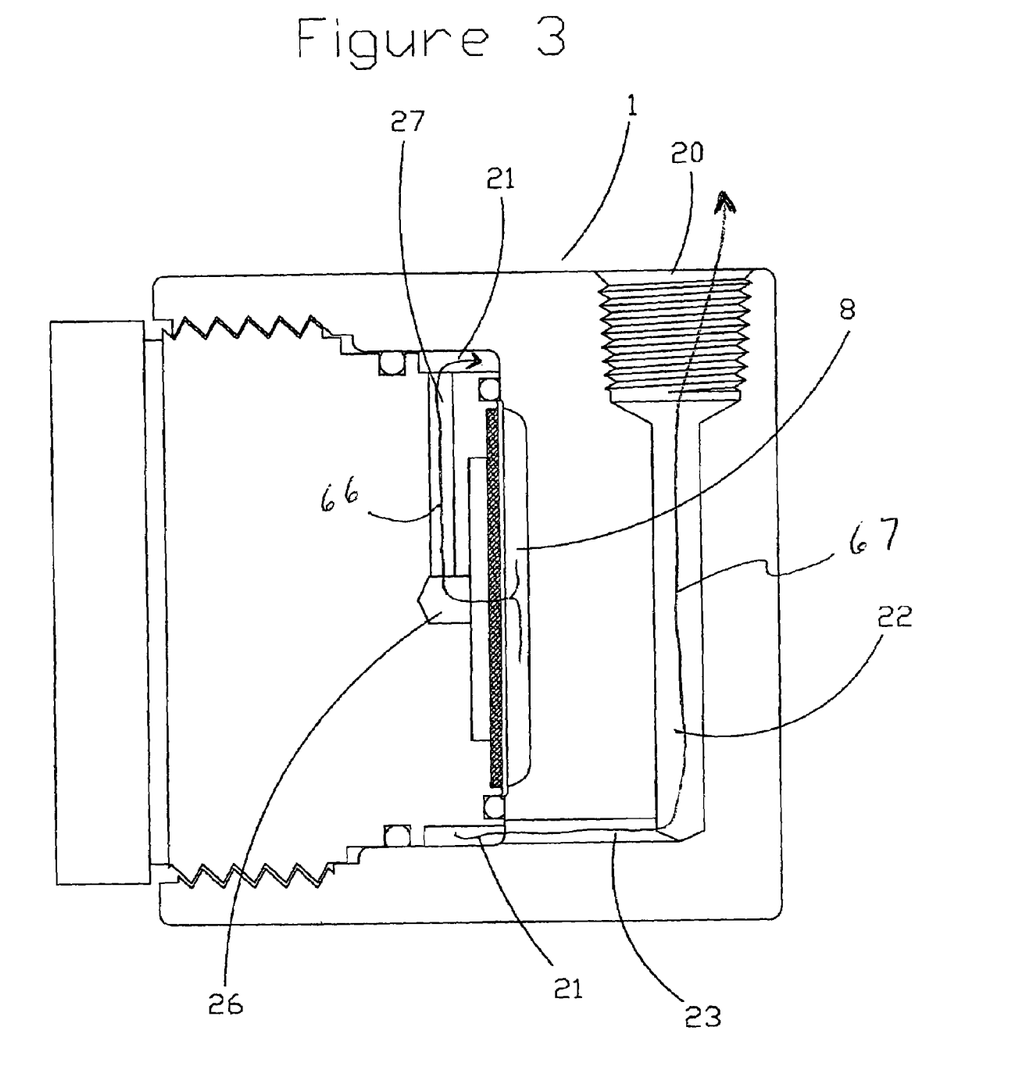
FIG. 3 is a side, partially cut-away view of the housing of FIG. 2, wherein the cover and body are rotated ninety degrees, with the outlet port shown.

Referring to FIG. 3, fluid from sample cavity 18 flows 66 through the sheet of phase-separation material 4, support plate 7 and into sample cavity 8, vertical passage 26, passage 27, and into cavity 21 (FIG. 2). From cavity 21 (FIG. 3) fluid flows 67 into passage 23 and passage 22 wherein it exits the housing by way of outlet port 20.

In cases where the sheet of phase separation material 4 is a phase separating membrane, liquid separated by the membrane 4 collects in the lower end 42 of cavity 18, flows 67 into passage 17 therein joining the fluid stream exiting from bypass port 16. Thus, a third purpose for the bypass port 16 is to facilitate the removal of materials rejected by sheet of phase-separating material 4 from the housing.

In summary, sample fluid enters housing 1 by way of inlet port 15. A portion of this fluid along with materials rejected by inertial tube 24 and sheet of phase-separation material 4 exits from bypass port 16. The second portion of fluid entering housing 1 flows through phase-separating material 4 and exits from outlet port 20. Fluid exiting from outlet port 20 is free of solid and liquid particles rejected by sheet of phase-separating material 4.

The above invention accomplishes several objectives. First of all, it provides a housing 1 for the sheet of phase separating material 4 which does not require tools to disassemble. Second, it does not require the disconnection of any tubing or fittings when the cover 2 is removed to access the phase-separating material 4 for inspection or exchange. Thirdly, the present invention also provides inertial pre-separation of phases so as to reduce the exposure of phase-separating material 4 to gummy, sticky or particle laden fluids. Fourthly, the construction of the present invention is reduced to two basic components, cover 2 and body 3.

Figure 5:
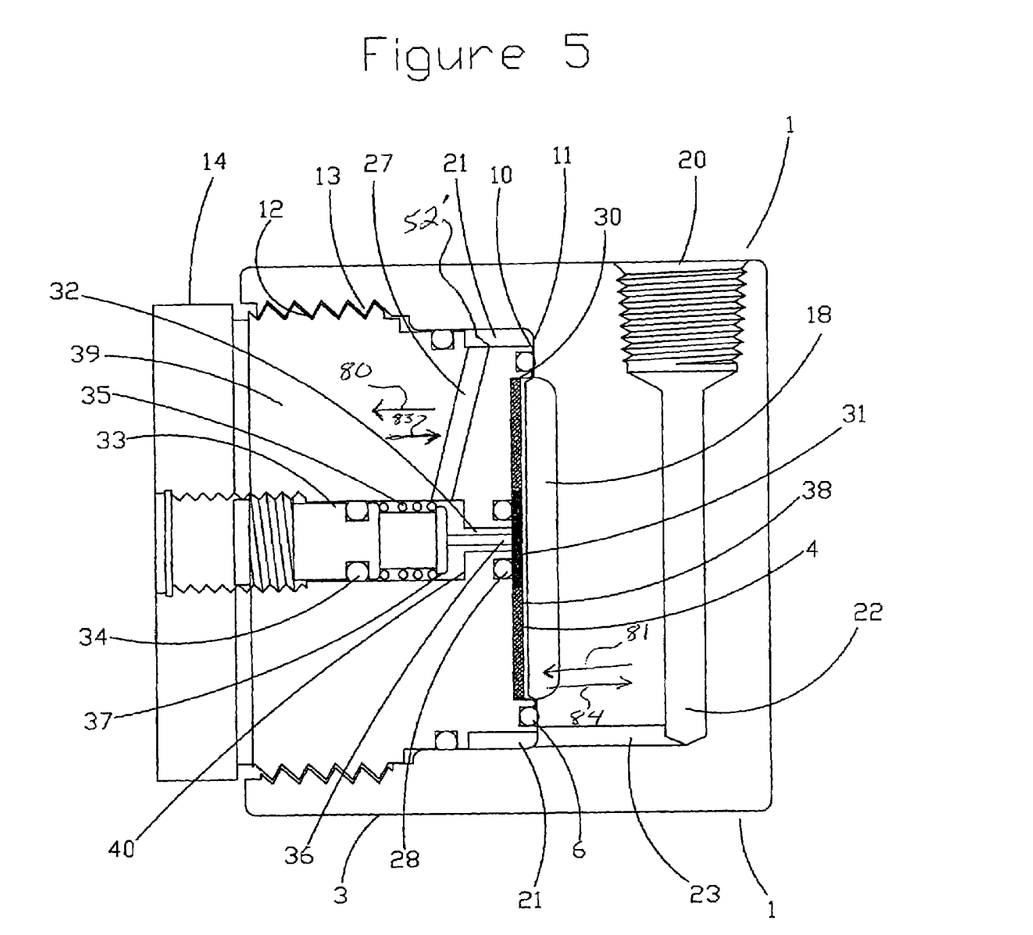
FIG. 5 is a side, cut away view of the housing of FIG. 4, wherein the internal valve of the cover is shown in a closed position.

Reference is made to the second embodiment of the current invention shown in FIGS. 4 and 5. Body 3 is identical in design to that of the first embodiment shown in FIG. 3. However, cover 39 differs from cover 2 (FIG. (1b) in that it contains an internal valve for the purpose of controlling or shutting off completely the fluid flow through the sheet of phase-separating material.

As shown, the cover 39 of the alternative embodiment of the invention has a bore 72 formed in the cover, said bore 72 having an inner diameter 69 having an opening 73 which ideally is threaded 74, the bore further comprising a smooth section 75 having an adjustment nut assembly 33 having an O-ring seal 34 situated about its perimeter and engaging the inner diameter 72 of the bore to seal same, said nut assembly 33 slidingly communicating in biased fashion (via spring 35) with pin plate 37, which has a pin 36 extending therefrom engaging support plate 38 situated in sample cavity 29. Adjustment nut assembly 33 may be adjusted via threaded portion 76 engaging threads 74.

Continuing with a description of valve 70, pin 36 passes through passage 32, which has an inner diameter greater than, pin to facilitate the selective passage of fluid there through, which passage 32 communicates with passage 27, then on to cavity 21, where it there is provided a passage about the perimeter 52 of cover (still contained in cavity 21 as earlier discussed). Passage 23 then communicates with cavity 21, which passage 23 leads to passage 22, then outlet port 20.

Figure 4A:
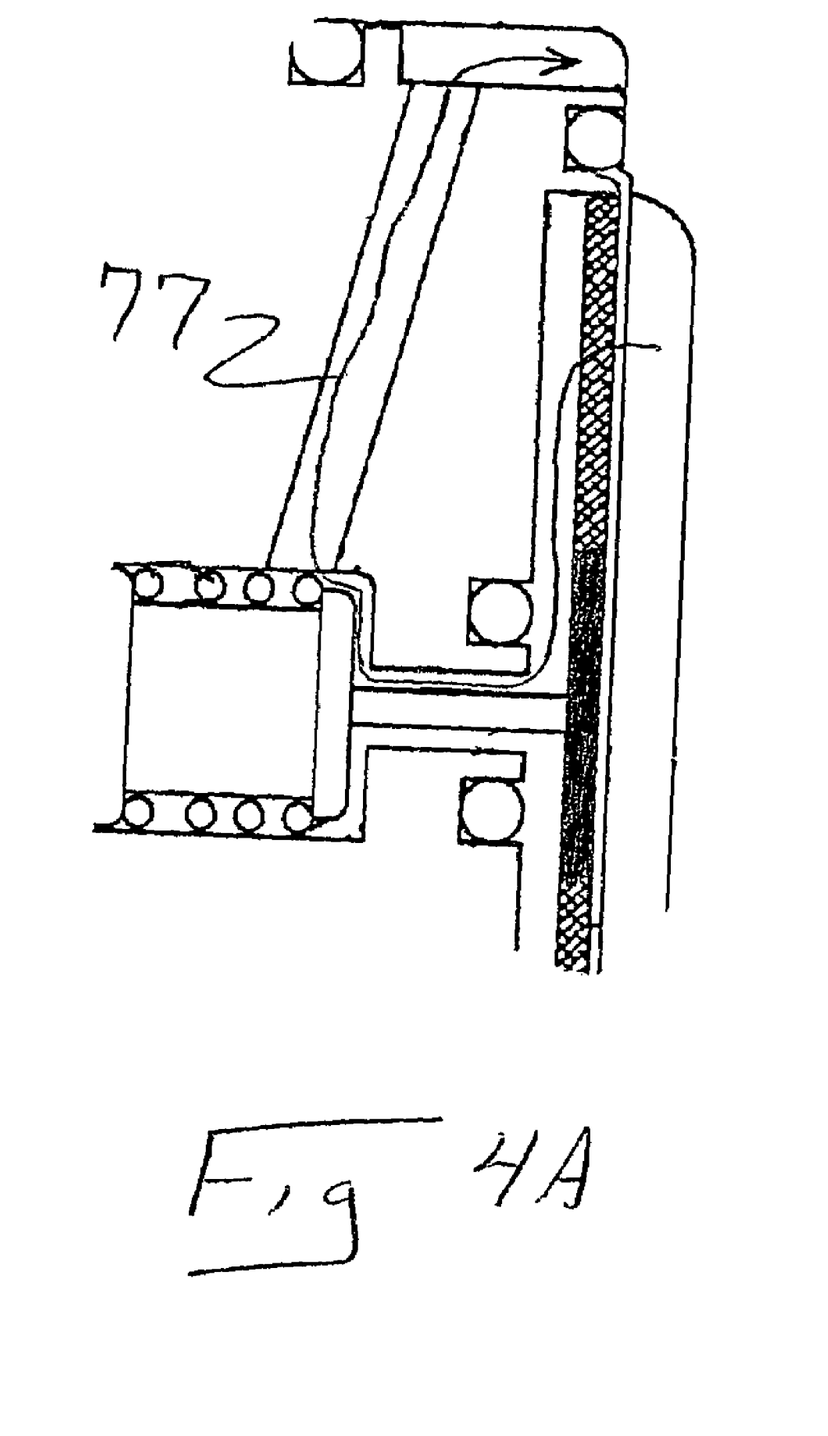
FIG. 4A is a close-up, partial, cut-away view of the housing of FIG. 4.

Referring to FIGS. 4 and 4A, in operation, sample fluid arrives in sample cavity 18 in the manner previously described for the first embodiment. Sample fluid flows 77 (FIG. 4A) from sample cavity 18, through sheet of phase-separating material 4, porous or perforated support plate 28, sample cavity 29, passage 32, around pin plate 37, passage 27, cavity 21, the about the perimeter 52' of cover (still contained in cavity 21) where the fluid then flows 78 through passage 23, passage 22 then exits from housing 1 by way of outlet port 20.

Continuing with FIGS. 4 and 5, in operation, the differential fluid pressure 79, 79' across sheet of phase-separating material 4 will increase as a result of (a) increases in fluid flow rate through the sheet of phase-separating membrane; (b) flow restriction in the sheet of phase-separating material resulting from the presence of liquids, gummy material or other forms of contaminations.

Under normal fluid flow conditions, a differential pressure is always present between the upstream and down stream surfaces of the sheet of phase-separating material 4. Said differential pressure 79, 79' exerts a force upon support plate 38, said force is then transmitted to spring 35 by way of pin 36, and pin plate 37. Spring 35 is compressed 80 as said force is increased as a result of an increased differential pressure. The force exerted by spring 35 is adjusted by rotating adjustment nut assembly 33.

Pin plate 37 travel away from spring 35 is limited by surface 40. Under normal operating conditions, force exerted by spring 35 against the pin plate 37 is preset to a desired value. In the case wherein the sheet of phase-separating material is a phase separating membrane the spring force is adjusted to a value which will prevent excessive differential fluid pressure across the membrane surfaces. Otherwise said differential pressure could cause liquid to be forced through the membrane, which is undesirable.

With pin plate 37 against surface 40, pin 36 travel is limited and support plate 38 is at its extreme position away from bottom surface 41 of sample cavity 29. The support plate will remain in that position from a condition of zero fluid flow to a condition wherein the differential pressure across the sheet of phase-separating material exerts a force greater in magnitude then the force exerted by spring 35. During this interval, fluids flow freely from sample cavity 29 to outlet port 20 (as shown in FIGS. 4 and 4A).

However, should the differential pressure tend to increase beyond that point, the force transmitted to spring 35 is increased thereby compressing 80 spring 35. As that occurs the distance between the un-perforated center section 31 of support plate 38 and internal valve o-ring 28 is diminished 81 resulting in increasing resistance to fluid flow between sample cavity 29 and passage 32.

Said distance is reduced to a point, which will reduce the fluid flow to a value, which is sufficient to limit the differential pressure across the sheet of phase-separating membrane to the preset value.

In cases where no amount of fluid flow can occur without exceeding said preset limit the un-perforated center section 31 of support plate 38 will contact internal valve o-ring 28 thereby shutting off fluid flow completely between sample cavity 29 and passage 32. Such a case can result when a liquid is present in sufficient amount on the surface of a phase-separating membrane, saturating the membrane and preventing the flow of fluid there through (as shown in FIG. 5).

When the differential pressure across the sheet of phase separating membrane lowers below the preset value, the force 83 exerted by spring 35 will force the un-perforated center section 31 of support plate 38 away 84 from internal valve o-ring 28. This will allow fluid flow to resume between sample cavity 29 and outlet port 20 (as shown in FIGS. 4, 4A).

Exemplary Specifications

Housing material: 316 Stainless Steel
Measurement of assembled unit 2.3" H×3.5" Diameter
Porous support plate:
2.05" diameter×0.032" thickness
Perforations are 0.062" diameter holes on 3/32" centers
0.438" Diameter circles in center of support is un-perforated in valve embodiment
Operational pressure: 2000 PSI
Differential pressure range 2-5 PSI
Sample flow rate: 5-8 liters/min
Bypass flow rate—varies with applications; approximate range from 1-20 liters per minute.
Exemplary sample source: Natural Gas; or Process fluids from chemical plants and refineries.
Maximum temperature: 105 degrees F. for type 5 & BTU membrane; 300 degrees F. for hi-flow backed membrane
O-rings: Viton
Internal volume:
  Total with liquid block: 9.1 cc
    Upstream of membrane: 5.4 cc
    Downstream of membrane: 3.7 cc
Applications:
Gas sampling conditioning for spot, composite, or continuous periods;
removes liquid entrainment;
Reduces condensation potential;
Reduces adsorption;
Analyzer protection against liquids;
GC's, Mass Specs, O2, H2S, Moisture and others
High pressure sampling processes Listing of Elements 1 Housing
2 Cover
3 Body
4 Sheet of phase-separating material
5 End of cover
6 Retention o-ring
7 Support plate
8 Sample cavity
9 O-ring
10 Lower end surface
11 Interior surface
12 Male threads
13 Female threads
14 Hand grip
15 Inlet port
16 Bypass port
17 Passage
18 Sample cavity
19 a & b passage
20 Outlet port
21 Cavity
22 Passage
23 Passage
24 Inertial tube
25 Inertial tube end
26 Vertical passage
27 Passage
28 Internal valve o-ring
29 Sample Cavity
30 Side wall
31 Center section of support plate
32 Passage
33 Adjustment nut assembly
34 Adjustment nut seal
35 Spring
36 Pin
37 Pin plate
39 Support plate
40 Cover
41 Surface
42 Bottom surface of sample cavity 29
43 Lower end of cavity 18
50 Main cavity
51,' First, Second ends
52 Outer Perimeter
53 ID
54 Edge of phase separation material
55 Groove
56 First, second sides
57 Groove
58 First, second sides
59 Sample fluid enters
60 Reverses
61 Out of housing
62 Flows
63,' Flows
64 Separated particles
65 Into sample cavity
66 Through sample cavity
67 Liquid flows
68
69 ID 70 Valve
71,' First, second ends
72 Bore
73 Opening
74 Threaded
75 Smooth section
76 Piston
77 Fluid flows
78 Flows out
79 Differential fluid pressure
80 Compressed
81 Dimmished
82 Away
83 Force
84 Away The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A valve comprising a sealing material and a surface actuated to a partially closed or closed position by a force resulting from a differential pressure across opposing sides of a diaphragm wherein the source of differential pressure is the result of a pressure drop across a sheet of phase-separating material.

2. The valve of claim 1 said sheet of phase-separating material forms said diaphragm.

3. The valve of claim 1 wherein said diaphragm is situated in a phase separating housing.

4. The invention of claim 3, wherein said housing comprises:
   a. a body having fluid entry and exit ports; a cavity for receiving a cover, said cavity having an inside diameter, and passages for fluid communication internal to the housing, and
   b. a cover having a for receiving and supporting the sheet of phase-separating material, said cover formed to engage said body in fluid impermeable fashion, said cover having an outside diameter.

5. The invention claim 4 wherein there is further provided in said housing an internal fluid passage formed between an outside diameter of the cover and the inside diameter of the cavity within the body.

6. The invention of claim 4 wherein said housing further comprises an inertial tube formed to separate particles from a sample fluid.

7. The invention of claim 6 wherein said cover of said housing engages said body via threaded engagement.

8. The invention of claim 4 wherein said housing further comprises a perforated plate formed to support said phase-separating material.

9. The invention of claim 3, wherein said housing comprises:
   a body having a main cavity formed therein;
   a cover having first and second ends, said first end of said cover formed to engage said body at said main cavity, said cover having;
   a first sample cavity formed in said body, said first sample cavity situated between said first end of said cover and said body, said first sample cavity formed to receive a stream of fluid from said housing; and
   a second sample cavity formed in said first end of said cover.

10. The invention of claim 9, wherein said housing has situated therein a fluid permeable support having first and second sides, said first side of said fluid permeable support communicating with said second sample cavity, said second side of said fluid permeable support formed to support said phase separating material; whereby, upon directing a fluid stream from said housing to said first sample cavity, a portion of said fluid stream passes through phase separation material and said fluid permeable support into said second sample cavity, so as to provide a filtered fluid stream, which filtered fluid stream may be directed out of said body.

11. The invention of claim 10, wherein said phase separating material comprises a filtration medium.

12. The invention of claim 11, wherein said cover and body of said housing are sealed about said first and second sample cavities by an O-ring.

13. The invention of claim 12, wherein said cover of said housing threadingly engages the cavity formed in said body.

14. The invention of claim 11, wherein said body of said housing has formed therein an inlet passage for the flow of unfiltered fluid into said body, said inlet passage having situated therein an inertial tube having first and second ends, said first end of said inertial tube communicating with said inlet passage formed in said body, said second end of said inertial tube situated within a secondary passage, said secondary passage in longitudinal alignment with said inertial tube.

15. The invention of claim 14, wherein said secondary passage has first and second ends, said first end of said secondary passage communicating with a bypass port, said second end of said secondary passage communicating with said first sample cavity.

16. The invention of claim 15, whereby, upon a flow of fluid exiting said second end of said inertial tube, fluid flowing to said second end of said secondary passage abruptly changes direction, providing a degree of inertial pre-separation of particulate matter situated in said fluid.

17. The invention of claim 15, wherein fluids which do not pass through said phase separating material collect in said first sample chamber.

18. The invention of claim 17, wherein there is further provided a drain passage running from said first sample chamber to said bypass port, formed to draining fluids which collect in said first sample chamber.

19. The invention of claim 10, wherein said cover has formed therein a first exit passage for the passing of said filtered fluid stream out of said cover and into said body.

20. The invention of claim 19, wherein said body has formed therein a second exit passage for the passing of said filtered fluid stream from said first exit passage out of said body.

21. The invention of claim 20, wherein said fluid permeable support is formed to be dynamically positionable within said second sample cavity whereby pressure applied to said first side of said fluid permeable support actuates said surface so as to decreases the flow of filtered fluid to said first exit passage.

22. The invention of claim 21, whereby a predetermined pressure applied to said first side of said fluid permeable support actuates said surface to interrupt the flow of filtered fluid to said first exit passage.

23. The invention of claim 22, wherein there is further provided in said valve a biased support pin formed to engage said fluid permeable support.

24. The invention of claim 23, wherein said biased support pin is spring biased.

25. The invention of claim 24, wherein the bias is adjustable.

26. The invention of claim 25, wherein said biased support pin has first and second ends, said first end engaging said second side of said fluid permeable support, said second end of said biased support pin engaging a pin plate, and whereby said spring engages said pin plate.

27. The invention of claim 26, wherein said support pin passes through said first exit passage.

28. The invention of claim 26, wherein there is further provided a fluid impermeable seal situated about said first exit passage in said second sample cavity.

29. The invention of claim 28, wherein said fluid impermeable seal comprises an O-ring.

30. The invention of claim 28, whereby, upon said second side of said fluid permeable support engaging said fluid impermeable seal, flow of filtered fluid to said first exit passage is interrupted.

31. The invention of claim 30, whereby upon said second side of said fluid permeable support dis-engaging said fluid impermeable seal, flow of filtered fluid to said first exit passage resumes.

32. The valve of claim 1 wherein the diaphragm is external to a phase-separating housing.

33. The valve of claim 1 wherein the sealing material is an o-ring.

34. The valve of claim 1 wherein said surface further comprises a support plate for a sheet of phase-separating material.

35. The valve of claim 1 wherein said sealing material and surface are constructed of metal.

36. A valve, comprising:
a sealing material having an underlying, fluid permeable support surface having first and second sides, said first side of said fluid permeable support surface formed to engage a sealing material, said second side formed to support a filtration medium;
biased positioning means for positioning said support surface;
whereby said biased positioning means is calibrated so that a predetermined differential pressure associated with said first and second sides of said support surface engages said bias means to position said first side of said fluid permeable support surface in one of open, partially closed, or closed positions.

37. The valve of claim 36, wherein the source of differential pressure is the result of a pressure drop across a phase separating membrane.

38. The valve of claim 36 wherein a sheet of phase-separating material functions as a diaphragm.

39. The valve of claim 38 wherein said diaphragm is situated in a phase separating housing.

40. The valve of claim 38 wherein said diaphragm is external to a phase-separating housing.

41. The valve of claim 36 wherein said sealing material is an o-ring.

42. The valve of claim 36 wherein said surface comprises a support plate for a sheet of phase-separating material.

* * * * *